United States Patent [19]

Faler

[11] Patent Number: 4,847,432
[45] Date of Patent: Jul. 11, 1989

[54] METHOD FOR THE PURIFICATION OF ION EXCHANGE RESINS USED IN THE PRODUCTION OF BISPHENOL A

[75] Inventor: Gary R. Faler, Scotia, N.Y.

[73] Assignee: General Electric Company, Schenectady, N.Y.

[21] Appl. No.: 137,983

[22] Filed: Dec. 28, 1987

[51] Int. Cl.$^4$ .................. C07C 39/16; C07C 39/12
[52] U.S. Cl. ............................. 568/727; 568/724; 568/728
[58] Field of Search ............... 568/726, 727, 728, 724

[56] References Cited

U.S. PATENT DOCUMENTS 3,172,916  3/1965  Wagner ........................ 568/728
3,394,089  7/1968  McNutt et al. ............... 568/728
4,400,555  8/1983  Mendiratta .................. 568/727

FOREIGN PATENT DOCUMENTS 849965  9/1960  United Kingdom .............. 568/727

OTHER PUBLICATIONS

"Neutralization of Impurities Formed During Manufacture and Separation of Bisphenol A Catalyzed by Cation Exchangers".
Kiedik, Maciej et al., (Instytut Ciezkiej Syntezy Organicznej "Blachownia"); Pol. PL 130,206 (Cl. C07C37/86), Apr. 25, 1986, Appl. 224,958, Jun. 1980; 3 pp.; Abstract No. Chem (107)176628c.

Primary Examiner—Werren B. Lone
Attorney, Agent, or Firm—Mary Ann Montebello; James C. Davis, Jr.; William H. Pittman

[57] ABSTRACT

A method for treating a sulfonic acid-containing ion exchange resin to remove destabilizing impurities therefrom is disclosed. The method comprises contacting the resin with a base, followed by contact with a strong acid. The treated ion exchange resin is particularly suitable for use as a catalyst in the preparation of bisphenol A.

4 Claims, No Drawings

METHOD FOR THE PURIFICATION OF ION EXCHANGE RESINS USED IN THE PRODUCTION OF BISPHENOL A

This invention relates generally to the preparation of bisphenol A, and more particularly to the treatment of ion exchange resin catalyst systems frequently used in such preparation.

2,2-bis(4-hydroxyphenyl)propane, commonly referred to as biphenol A or BPA, is an important intermediate for the preparation of various polymeric materials, such as polycarbonates and epoxy resins. It is usually produced on a commercial scale by the acid-catalyzed reaction of phenol with acetone. One particularly attractive catalyst system employs an ion exchange resin, such as a sulfonated polystyrene material (a cationic exchange resin), often in combination with a mercaptan as a reaction rate accelerator. The primary benefit associated with this type of catalyst system is the ease with which it can be removed from the product mixture after use.

The product mixture resulting from the above-described reaction generally contains bisphenol A, excess phenol, acetone, water, and phenol-acetone condensation by-products. Bisphenol A is often isolated from this reaction mixture as a bisphenol A-phenol adduct, via filtration techniques. Additional bisphenol A may be recovered from the mother liquor of this filtration by various distillation techniques.

Distillation of the mother liquor during this process often results in a substantial loss of the bisphenol A product. Furthermore, the mother liquor often becomes contaminated with darkly colored materials which can be very difficult to remove during subsequent purification processes. It is thought that product loss and undesirable color formation are caused in part by the acid-catalyzed cracking which occurs during the distillation step, in which the mother liquor is subjected to temperatures in the range of about 200°–240° C. Low molecular weight sulfonic acids present in the ion exchange resin apparently are leached therefrom and into the mother liquor. The sulfonic acids can cause decomposition of the bisphenol A product at elevated temperatures into phenols and various oligomers of isopropenyl phenol, derivatives of the latter apparently forming the highly colored materials.

Since both low product yield and the presence of colored impurities can greatly detract from the utility of cationic exchange resin processes to form bisphenol A, various procedures have been undertaken to remove such impurities or to minimize their harmful effects. One such procedure is described in U.S. patent application Ser. No. 104,602, filed Oct. 5, 1987, and assigned to the assignee of the present invention. The disclosure of U.S. patent application Ser. No. 104,602 is incorporated herein by reference. The technique described in that application stabilizes the mother liquor by contacting it with a basic anion exchange resin at a temperature in the range of about 45° C.–125° C. Upon contact with the anion exchange resin, acidic impurities are removed by salt formation therewith. The resin may be regenerated by treatment with an aqueous base.

The procedure described in U.S. patent application Ser. No. 104,602 can be described as an "on line" treatment. An alternative procedure which could accomplish the same objectives might be one taking place at an earlier stage in the overall process. It is therefore an object of the present invention to provide a process for improving the isolated yield of bisphenol A prepared from an ion exchange resin-catalyzed reaction, while also minimizing or substantially preventing the formation of darkly colored materials in the product mixture.

DESCRIPTION OF THE INVENTION

The present invention is a method for treating a sulfonic acid-containing ion exchange resin, comprising contacting the resin with a base, followed by contact with a strong acid.

Any conventional ion-exchange resin having appended sulfonic acid groups may be treated according to the present invention. Some of these are described in A. Mendiratta's U.S. Pat. No. 4,400,555, incorporated herein by reference. The polymer matrix of the resin itself may be formed of a variety of materials, such as polystyrene; copolymers of styrene and divinylbenzene; acrylic; phenolic; and Teflon ®-type materials such as tetrafluoroethylene fluorocarbon or fluorinated ethylene-propylene polymers.

Illustrative sulfonated polystyrene resins frequently used are formed of copolymers of styrene and divinylbenzene, the latter compound generally being employed as a cross-linking agent at a level of about 1% to about 50% by weight, based on total resin weight. Specific examples of commercially available sulfonic acid-containing resins are Amberlite ® and Amberlyst ® resins, available from Rohm & Haas Company, and Dowex ® resins, available from Dow Chemical Company. These ion exchange resins are often partially modified by reacting the acidic groups with mercaptoalkylamines, with a mercapto alcohol, or with an akylamine precursor such as a thiazolidine compound. For example, about 5% to about 35% of the acid sites on the resin can be modified by reaction with a mercapto derivative, as specified above. Such a modification does not affect the results of treatment by the present invention, with the proviso that it follow, rather than precede, such treatment.

A wide variety of bases may be used in the first step of the process. Strong bases such as sodium hydroxide, potassium hydroxide, lithium hydroxide, and ammonia are preferred because of their ability to neutralize strong acid groups more quickly. Sodium hydroxide is especially preferred in certain embodiments because of its low cost, relative availability, and compatibility with certain reaction processes utilizing the ion exchange resin, e.g., the preparation of bisphenol A.

For ease in treatment, some of the bases are utilized in the form of a solution, e.g., about 1%–20% by weight sodium hydroxide dissolved in water.

Generally, about 3 to 5 milliequivalents of base are required for every milliequivalent of acid present in the sulfonated ion exchange resin, although greater amounts could be used. 4 milliequivalents of base is the preferred amount. It is thought that this amount of base is sufficient to neutralize all of the sulfonic acid sites present in the ion exchange resin.

The method of contacting the ion exchange resin with the base is not particularly critical. One suitable technique is to immerse the resin in an aqueous solution of the base. In those circumstances in which the ion exchange resin is already installed in a reactor, contact with the base can be conveniently carried out by simply feeding the base or solution thereof in a stream through the reactor in the same manner that reactants are fed. For example, washing the resin with a solution of the base flowing continuously therethrough at a weight-hourly-space-velocity (WHSV) of about 0.5 hr.$^{-1}$ to about 30 hr.$^{-1}$ is generally sufficient. This contact may be followed by a wash with deionized water. Regardless of method of contact, the entire resin should come into contact with the base, thereby ensuring that sulfonic acid groups in the interior portions of the resin matrix are also neutralized.

The resin is usually subjected to a water wash after contact with the base, although this step is not critical.

Following contact with the base (and optionally, the water wash), the resin is contacted with a strong acid. Exemplary strong acids are hydrochloric acid, sulfuric acid, nitric acid, and para-toluenesulfonic acid. The acid can be supplied in the form of an aqueous solution, as is well-known in the art, e.g., about 1% to 10% hydrogen chloride in water; about 2% to 10% sulfuric acid in water; about 1% to 20% nitric acid in water, and the like. In some embodiments, sulfuric acid is preferred because of its availability and low cost. In other embodiments, especially where the resin being treated is in contact with or adjacent to metallic equipment, nitric acid is preferred because of the decreased potential for corrosion.

Generally, about 3 to 5 milliequivalents of the strong acid are used for every milliequivalent of sulfonic acid neutralized by the base, although greater amounts could be used. 4 milliequivalents of the strong acid is the preferred amount. It is thought that this amount of acid is sufficient to reacidify the sulfonic acid groups of the resin which had been neutralized during contact with the base.

Contact with the strong acid may be effected by the same techniques used for the base, e.g., by immersion or by flow-through at WHSV values of about 0.5 hr.$^{-1}$ to about 30 hr.$^{-1}$. The most appropriate amount of strong acid may easily be determined by taking a measurement of reacidification. For example, sodium hydroxide could be mixed with a sample of the resin, followed by filtering and then backtitrating to determine how much sodium hydroxide was consumed.

After being treated, the purified ion exchange resin may again be washed with deionized water and then immediately installed in a reactor system; or may be rinsed, dried, and then stored for future use.

Although generally not necessary, multiple base/acid cycles might be used, rather than the one-cycle treatment described above. Water washes could be used between each cycle.

This invention includes within its scope a method for preparing substantially pure bisphenol A in high yield by the use of a sulfonic acid-containing ion exchange resin catalyst treated as described above. The amount of base as described above for such catalyst treatment is thought to be sufficient to neutralize substantially all of the sulfonic acid groups in the resin. The soluble portion of these neutralized groups are removed with the wash streams. As also described above, the strong acid subsequently employed is present in an amount thought to be sufficient to reacidify the remaining neutralized sulfonic acid groups.

The bisphenol A-containing mother liquor will remain thermally stable during subsequent distillation because the ion exchange resin had been treated in this manner.

Considerable mention has been made here of the use of the treated ion exchange resin as a catalyst in the preparation of bisphenol A. However, it is to be understood that this resin may be used to catalyze reactions which form a variety of other dihydroxyaromatic compounds, as described in U.S. Pat. No. 4,400,555. Those of ordinary skill in the area of chemical synthesis understand that reactions which form compounds in any way similar to bisphenol A may also result in product degradation due to the undesirable leaching of acid groups from the ion exchange resin. This invention will prove useful in those reaction systems, and may also be valuable in other reactions catalyzed with this type of ion exchange resin, e.g., alkylation reactions such as esterification.

The following examples illustrate the process of this invention. All values and ratios are by weight, unless other indicated.

Example 1: Preparation of Control Ion Exchange Resin Catalyst 175.0 g of a sulfonated polystyrene ion exchange resin (IER) cross-linked with 1% divinylbenzene was added to a glass column filled with deionized water. The catalyst was washed with 1600 mL of deionized water at a weight-height-space-velocity (WHSV) of 25.6 hr.$^{-1}$. The effluent in the early part of the washing procedure was found to be acidic to litmus paper, but was neutral at the end of the procedure. The resin bed was subsequently drained and employed in a bisphenol A reactor without any further treatment.

Example 2: Preparation of an IER Treated by the Present Invention 91.0 g of a sulfonated ion exchange resin like that of Example 1 was added to a glass column filled with deionized water. The catalyst was washed in a continuous fashion at a WHSV of 25 hr.$^{-1}$ with the following reagents in sequence:
(1) 150 mL H$_2$O
(2) 150 mL 5.0% NaOH
(3) 100 mL H$_2$O
(4) 150 mL 2.5% H$_2$SO$_4$
(5) 100 mL H$_2$O
(6) 150 mL 5.0% NaOH
(7) 100 mL H$_2$O
(8) 150 mL 2.5% H$_2$SO$_4$.

After the final sulfuric acid wash, the resin was washed with water until the effluent was neutral to litmus paper. The resin bed was subsequently drained and then employed in a bisphenol A reactor without any further treatment.

Example 3: Use of Treated Ion Exchange Resin in a Continuous Reactor System 80 g of the wet ion exchange resin prepared in Example 2 was charged to a 1"×11" glass tube equipped with a heated jacket. 300 g of anhydrous phenol was passed through this catalyst in an up-flow fashion to dehydrate the bed. The reactor feed was then switched to a 14/1 (molar) phenol/acetone mixture containing 420 ppm of 3-mercaptopropionic acid. This feed mixture was passed through the catalyst bed at a WHSV of 0.522 hr.$^{-1}$, and at a temperature of 70° C. The bisphenol A reactor effluent was collected and subsequently subjected to a standard cracking procedure to determine the degree of thermal stability.

Example 4: Standard Cracking Procedure 163.0 g of a bisphenol A reactor effluent containing about 16.4% by weight bisphenol A was added to a 250 mL round bottom flask. The phenol was removed by distillation until the product temperature reached 210° C. An aliquot of the residue from the distillation pot was removed and analyzed via high pressure liquid chromatography to determine the amount of bisphenol A present. This reaction mixture was subsequently heated at reflux for a period of 4 hours. Another aliquot of residue was then removed and analyzed to determine the amount of bisphenol A remaining; from which the degree of cracking was determined.

Example 5: Batch Cracking Procedure 100 g of phenol was added to 50 g of the ion exchange resin treated according to Example 1. This mixture was then heated with gentle stirring at 70° C. for a period of 16 hours. The hot mixture was filtered through a fine filter. The molten phenol was treated with 16.0 g of bisphenol A and then subjected to the standard cracking test described in Example 4.

Tables 1 and 2 summarize the results obtained for a bisphenol A product stream prepared and evaluated according to the above examples:

TABLE 1

Effect of Treated Ion Exchange Resin on the Heat Stability of Bisphenol A - Batch Reaction Cracking Procedure[a]

| % Bisphenol A Cracking | |
| --- | --- |
| Control[b] | Treated IER[c] |
| 63 | None |

[a]Wet IER heated in phenol for 16 hours according to Example 5.
[b]IER washed only with water ($H_2O$/catalyst = 9.3).
[c]IER treated according to present invention (Example 2)

TABLE 2

Effect of Treated Ion Exchange Resin on the Heat Stability of Bisphenol A - Continuous Reaction Cracking Procedure

| Period of Continuous use with IER (days) | % Bisphenol A Cracking | |
| --- | --- | --- |
| | Control[a] | Treated IER[b] |
| 0[c] | 50.8 | 0.0 |
| 1 | 36.0 | 1.0 |
| 2 | 14.4 | No data |
| 3 | 8.4 | 0.0 |

[a]IER washed only with water ($H_2O$/catalyst = 9.3).
[b]IER treated according to present invention (Example 2)
[c]Bisphenol A added to phenol wash; resultant mixture subjected to cracking test according to Examples 3 and 4.

As shown in Tables 1 and 2, the use of the control IER resulted in severe cracking of the bisphenol A. Cracking decreased over time, apparently because the sulfonic acid groups were being leached out of the resin. In a commercial situation, the bulk of the phenol containing these acidic impurities would be recirculated, and cracking would continue to occur.

In contrast, the use of the IER treated by the present invention resulted in practically zero cracking over a three day period. In the actual experiment, the absence of bisphenol A cracking continued over a six day period.

Example 6: Determination of Tar Factor

The tar factor is a measurement of the color of a bisphenol A stream, color itself being indicative of the presence of impurities in the stream. Lower tar values are desirable because they indicate reduced color of the product stream. This color analysis technique is generally described in U.S. Pat. No. 4,400,555, referenced above. The catalysts were prepared and utilized as in Examples 1-3. In the present example, 5.0 g of the bisphenol A reaction effluent from the reaction system using the control IER and the IER of the present invention were each added to 50 mL of spectral grade methanol, followed by analysis via high pressure liquid chromatography. The absorbance at 350 nm in a 10 cm pathlength cell was determined, using a Varian Cary 219 spectrophotometer. The resulting values multiplied by a factor of 10 result in the tar factor values shown in Table 3.

TABLE 3

| | Tar Factor Values | |
| --- | --- | --- |
| | Use of Control IER | Use of Treated IER |
| Phenol Wash[a] | 1.13 | 0.74 |
| Bisphenol A Effluent | 3.92 | 2.28 |

[a]Phenol wash from Example 3.

Table 3 demonstrates a visual reduction in the color of the continuous reactor effluent when an IER resin was treated beforehand by the method of the present invention.

It has thus been demonstrated that the method of the present invention is successful in suppressing the decomposition of bisphenol A prepared by the ion exchange process. Moreover, the color of the bisphenol A product is substantially decreased.

While the invention is described with respect to several preferred embodiments, it will be apparent to those of ordinary skill in the art that certain modifications and changes may be made without departing from the broad teachings herein. It is thus intended that the foregoing disclosure be limited only by the claims appended hereto.

What is claimed is:

1. A method for preparing substantially pure bisphenol A in high yield by the use of a sulfonic acid-containing ion exchange resin catalyst, comprising first treating the resin by contact with a base and then a strong acid, followed by reaction of acetone and phenol in the presence of the resin to form the bisphenol A product.

2. The method of claim 1 wherein about 3 to 5 milliequivalents of the base are used for every milli-equivalent of sulfonic acid present in the ion exchange resin.

3. The method of claim 2 wherein about 3 to 5 milliequivalents of the strong acid are used for every milliequivalent of sulfonic acid neutralized by the base.

4. The method of claim 3 wherein the base is sodium hydroxide, and the strong acid is either nitric acid or sulfuric acid.

* * * * *